United States Patent [19]

Theeuwes et al.

[11] Patent Number: 5,312,389

[45] Date of Patent: * May 17, 1994

[54] OSMOTICALLY DRIVEN SYRINGE WITH PROGRAMMABLE AGENT DELIVERY

[76] Inventors: Felix Theeuwes, 1634 Fallen Leaf La.; Su Il Yum, 1021 Runnymead Ct., both of Los Altos, Calif. 94022

[ * ] Notice: The portion of the term of this patent subsequent to Sep. 29, 2009 has been disclaimed.

[21] Appl. No.: 863,649

[22] Filed: Apr. 3, 1992

Related U.S. Application Data

[63] Continuation of Ser. No. 605,593, Oct. 29, 1990, Pat. No. 5,151,093.

[51] Int. Cl.$^5$ ............................................. A61K 9/22
[52] U.S. Cl. .................................. 604/892.1; 604/141; 604/218; 424/472; 424/473; 222/389
[58] Field of Search ............... 604/892.1, 890.1, 891.1, 604/131, 140, 141, 150, 151, 156, 218, 235; 424/472, 473; 222/389

[56] References Cited

U.S. PATENT DOCUMENTS

| | | | |
|---|---|---|---|
| 2,674,619 | 10/1953 | Lundsted | 260/485 |
| 3,133,132 | 5/1964 | Loeb et al. | 264/49 |
| 3,173,876 | 3/1965 | Zobrist | 252/137 |
| 3,276,586 | 8/1963 | Rosaen | 210/90 |
| 3,325,357 | 6/1967 | Irani | 167/57 |
| 3,340,309 | 9/1967 | Weipert | 260/615 |
| 3,367,545 | 2/1968 | Cook | 222/389 |
| 3,504,041 | 3/1970 | Weipert | 260/615 |
| 3,541,005 | 11/1970 | Strathmann et al. | 210/19 |
| 3,541,006 | 11/1970 | Bixler et al. | 210/23 |
| 3,546,142 | 1/1971 | Michaels et al. | 260/2.1 |
| 3,604,417 | 9/1971 | Stolzenberg | 222/389 |
| 3,760,804 | 9/1973 | Higuchi et al. | 604/892.1 |
| 3,760,984 | 9/1973 | Theeuwes | 222/95 |
| 3,796,817 | 3/1974 | Aepli et al. | 426/287 |
| 3,845,770 | 11/1974 | Theeuwes et al. | 128/260 |
| 3,971,376 | 7/1976 | Wichterle | 128/260 |
| 3,987,790 | 10/1976 | Eckenhoff et al. | 128/260 |
| 3,995,631 | 12/1976 | Miguchi et al. | 604/892.1 |
| 3,995,632 | 12/1976 | Nakano et al. | 128/260 |
| 4,036,228 | 7/1977 | Theeuwes | 128/260 |
| 4,093,708 | 6/1978 | Zaffaroni et al. | 604/892.1 |
| 4,203,440 | 5/1980 | Theeuwes | 222/386.5 |
| 4,350,271 | 9/1982 | Eckenhoff | 604/892.1 |
| 4,410,328 | 10/1983 | Theeuwes | 604/892 |
| 4,723,958 | 2/1988 | Pope et al. | 604/890.1 |
| 4,740,197 | 4/1988 | Theeuwes | 604/892.1 |
| 4,814,181 | 3/1989 | Jordan et al. | 424/473 |
| 4,847,093 | 7/1989 | Ayer et al. | 424/473 |
| 4,865,845 | 9/1989 | Eckenhoff et al. | 604/892.1 |
| 4,969,884 | 11/1990 | Yum | 604/892.1 |
| 5,030,216 | 7/1991 | Theeuwes et al. | 604/892.1 |
| 5,128,145 | 7/1992 | Edgren et al. | 604/892.1 |
| 5,151,093 | 9/1992 | Theeuwes et al. | 604/892.1 |

OTHER PUBLICATIONS

"Modern Plastics Encyclopedia", vol. 46, pp. 62 to 70, 1969.

"Remington's Pharmaceutical Science", 14th Ed., pp. 1649 to 1968, 1970, published by Mack Publishing Mack Publishing Co., Easton, Pa.

(List continued on next page.)

Primary Examiner—C. Fred Rosenbaum
Assistant Examiner—C. Smith
Attorney, Agent, or Firm—Jean Marie Duvall; Steven F. Stone; Edward L. Mandell

[57] ABSTRACT

An osmotically driven syringe (20, 60) is disclosed which can be used to deliver a beneficial agent such as a drug, at varying pre-determined rates over multiple periods of time. The syringe (20, 60) is driven by an osmotic engine (10) having a shaped wall (12) containing an osmotic agent (17) and/or a gas generating means (19), such as an effervescent couple. The wall (12) is composed of a semipermeable and/or microporous material which is permeable to an external liquid (e.g., water) but which is substantially impermeable to the osmotic agent (17) and the gas generated by the gas generating means (19). The wall (12) has a passageway (13) therethrough to provide a flow path for the driving fluid generated by the engine (10). The osmotic agent(s) (17) and/or the gas generating means (19) are placed in the engine (10) in such a way as to drive engine (10) at different pumping rates ($R_1$, $R_2$) over sequential periods of time ($t_0$ to $t_1$ and $t_1$ to $t_2$).

31 Claims, 5 Drawing Sheets

OTHER PUBLICATIONS

"The Theory and Practice of Industrial Pharmacy", by Lachman, et al., pp. 197 to 225, 1970, published by Lea & Febiger, Philadelphia, Pa.

"Solubilization by Surface-Active Agents", by Elworth, P. H., et al, 1968, published by Chapman and Hall Ltd., London.

"Systemic Analysis of Surface-Active Agents", by Rosen, Milton J., et al, 1972, published by Wiley-Interscience Inc., Sydney.

"Encyclopedia of Polymer Science and Technology", vol. 13, pp. 477 to 486, 1970, published by John Wiley & Sons Inc., New York.

"The Theory and Practice of Industrial Pharmacy", by Lachman, L. et al., pp. 618 to 621, 1970, by Leas & Febiger, Philadelphia.

Chemical Principles Fourth Edition, Masterton & Slowinski pp. 298-300, 1977 W. B. Saunders Co.

OSMOTICALLY DRIVEN SYRINGE WITH PROGRAMMABLE AGENT DELIVERY

This application is a continuation of U.S. patent application Ser. No. 07/605,593 filed Oct. 19, 1990 now U.S. Pat. No. 5,151,093.

TECHNICAL FIELD

The invention pertains to an osmotically driven syringe for delivering an agent, and in particular for delivering a beneficial agent at a programmed delivery profile to an environment of use.

BACKGROUND ART

Over the past decade, much research has been devoted to developing new and useful devices for delivering beneficial agents to agent receptor environments of use. For example, Theeuwes U.S. Pat. No. 3,760,984 discloses an osmotic delivery device comprising an inner collapsible container carrying on its outer surface a layer of an osmotic solute and a surrounding layer of a polymer permeable to fluid and impermeable to solute. Wichterle U.S. Pat. No. 3,971,376 discloses a device comprising a capsule having a unitary wall formed of a substantially noncollapsible elastic material that maintains a constant volume and adapted to be implanted subcutaneously. A textile fabric may be imbedded in the capsule wall. The fabric strengthens the wall and acts as a reinforcement. Eckenhoff et al. U.S. Pat. No. 3,987,790 discloses another osmotic delivery device which contains an outer shape-retaining membrane which is sufficiently rigid to be substantially undeformed by the hydrostatic pressure exerted by water permeating through the membrane.

Higuchi et al. U.S. Pat. No. 3,995,631 discloses a device (FIG. 4) comprising an inner flexible bag containing a drug formulation. The bag separates the drug from an osmotically effective solute material. Both the drug and the solute are contained within a housing having an exterior wall that is, at least in part, semipermeable. Nakano et al. U.S. Pat. No. 3,995,632 discloses a similar device which incorporates a movable barrier within the housing. The barrier divides the housing into two compartments, one containing the solute and the other containing the drug. The solute-containing compartment has an exterior wall that is, at least in part, semipermeable. This compartment acts as an osmotic driver for the device.

Theeuwes U.S. Pat. No. 4,410,328 discloses an osmotically driven syringe/pump device. The osmotic driver in this device comprises a tablet of an osmotic solute, such as sodium chloride, coated with a semipermeable membrane having a fluid delivery orifice drilled therethrough. The influx of liquid into the osmotic engine, due to the homogeneous nature of the osmotic solute tablet, is constant and therefore the rate of delivery of solution from the osmotic engine into the driving compartment of the syringe is also constant. As a result, the syringe/pump device operates in a "steady state" or "tonic" mode which is characterized by a controlled although constant rate of drug delivery.

Pope et al U.S. Pat. No. 4,723,958 discloses an osmotically driven drug dispensing device. The delivery system provides an intermittent (i.e., on-off-on-off) drug delivery profile which is accomplished through the use of alternating layers of active drug and inert layers. In this device, similar to the device disclosed in U.S. Pat. No. 4,410,328, the influx of liquid into the osmotic driver, due to the homogeneous nature of the osmotic solute, is constant. Therefore, the rate at which the alternating layers are pushed out of the device is also constant. While this device provides some control over when the drug delivery pulses occur, there is no control over the rate at which the drug is delivered during the pulses.

Theeuwes U.S. Pat. No. 4,036,228 discloses an osmotic delivery device that uses a gas generating means, such as an effervescent couple, to deliver a drug which is insoluable in water at a controlled rate. The effervescent couple is osmotically active, causing water to premeate across the semipermeable outer wall. The water reacts with the effervescent couple to produce a gas which is pumped out of a delivery orifice. The pumped gas carries the insoluble drug to the desired environment of use.

While the above-described devices are useful for delivering many agents, and while they represent a valuable contribution to the delivery art, there has been a need in the art for a device which can deliver a beneficial agent to an environment of use at a continuous, controlled and variable rate of delivery.

Therefore, it is an object of the present invention to provide an osmotically driven syringe which can deliver a beneficial agent, such as a drug, to an environment of use at a controlled and non-constant delivery rate in order to optimize the treatment of a patient.

DISCLOSURE OF THE INVENTION

The present invention provides an osmotically driven dispensing device, and an osmotic engine therefor, for continuously delivering a beneficial agent to an environment of use. The device comprises a syringe housing having a movable piston therein, the piston dividing the syringe housing into a beneficial agent-containing compartment and a driving compartment. An osmotic engine is provided adjacent the driving compartment of the syringe. The osmotic engine comprises a shaped wall surrounding a means for forming a driving fluid including an osmotic solute which is soluble in the external liquid. A passageway is provided through the wall for delivering the driving fluid from the engine into the driving compartment of the syringe. At least a portion of the wall is comprised of a material that is permeable to an external liquid and has a sufficient degree of impermeability to the osmotic solute to create an osmotic pressure differential across the wall when the wall is exposed to the external liquid. In operation, the external liquid is imbibed through the semipermeable wall portion into the osmotic engine by the osmotic pressure differential. The imbibed liquid forms a solution of the solute and/or a gas which is pumped through the passageway into the driving compartment. The pumping of the solution and/or gas drives the piston to deliver the beneficial agent from the agent-containing compartment at a predetermined rate profile. The predetermined rate profile includes a first delivery rate over a first period of time and a second delivery rate over a second period of time, the second rate being unequal to the first rate.

The means for forming a driving fluid within the osmotic engine perferably comprises a tablet having a layer of a gas generating means and a layer of an osmotically active solute. The tablet produces two separate driving fluids; one is a gas produced by the gas generating means and the other is a solution of the osmotic solute. The gas generating means layer may be used to produce a pulse in the delivery rate profile of the osmotic engine. Optionally, a third layer of a different osmotically active solute may be employed within the osmotic engine.

BRIEF DESCRIPTION OF THE DRAWINGS

In the drawings and specification, like parts in related Figures are identified by like numbers.

MODES FOR CARRYING OUT THE INVENTION

Figure 1:
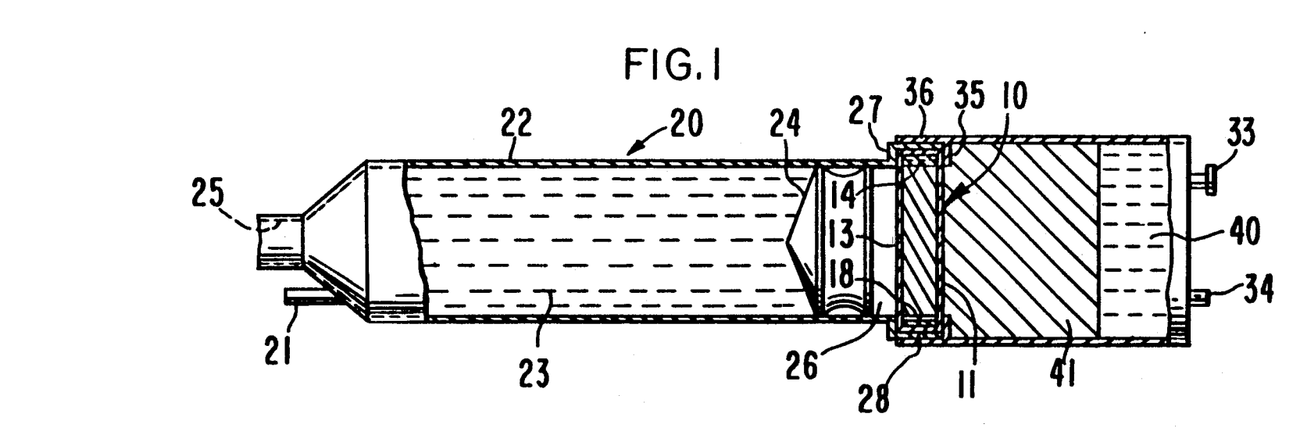
FIG. 1 is a cross sectional view of one embodiment of an osmotically driven syringe according to the present invention.
Figure 2:
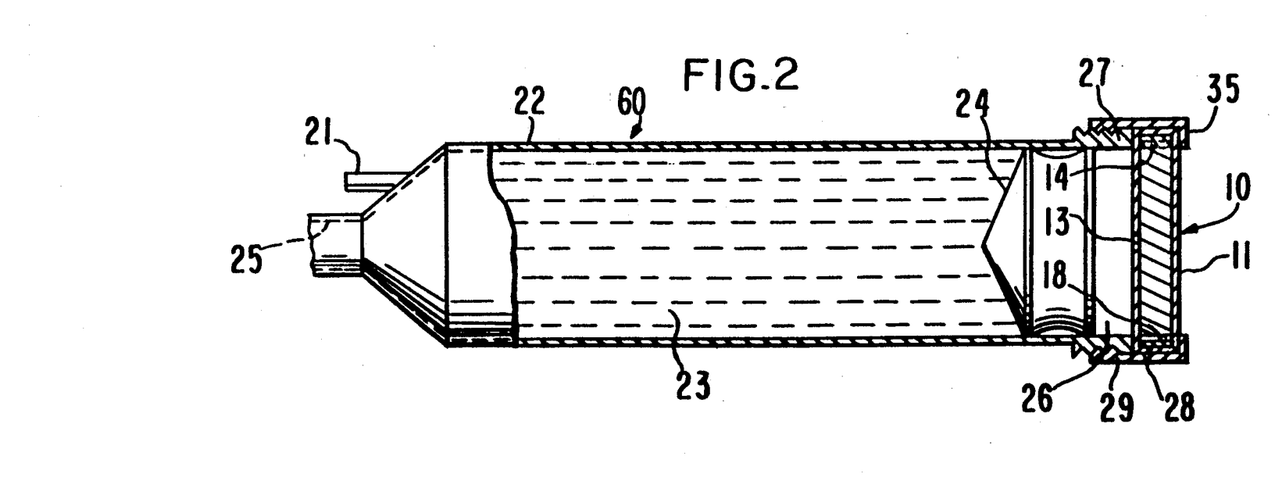
FIG. 2 is a cross sectional view of another embodiment of an osmotically driven syringe according to the present invention.
Figure 3:
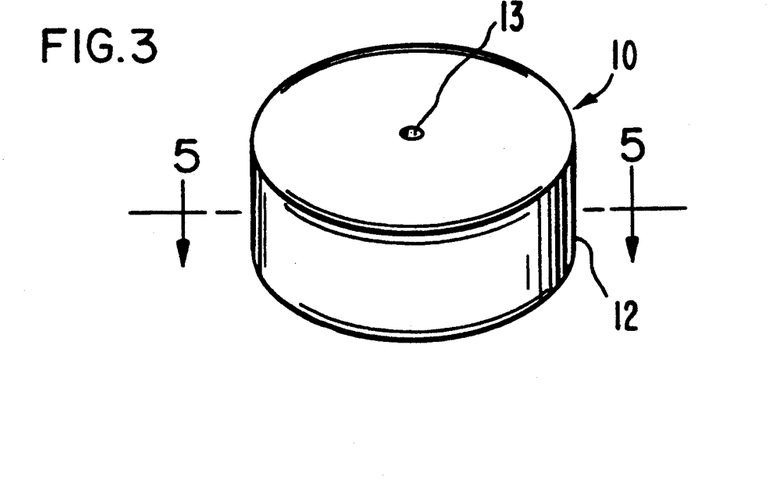
FIG. 3 is a perspective view of the osmotic engine shown in FIGS. 1 and 2.
Figure 4:
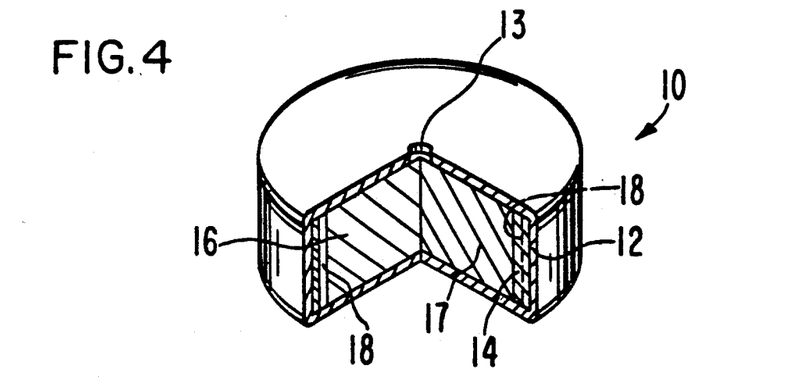
FIG. 4 is an opened view of the osmotic engine of FIG. 3 illustrating the internal structure of the engine.
Figure 5:
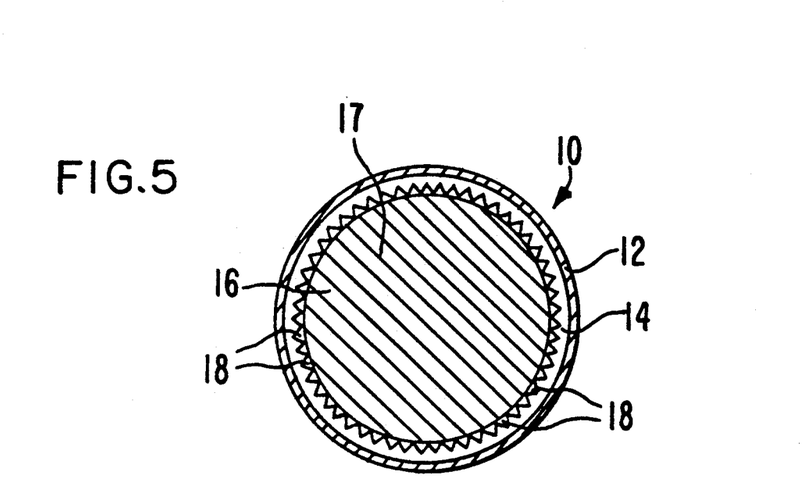
FIG. 5 is a cross sectional view of the osmotic engine shown in FIG. 3, taken along line 5—5.
Figure 6:
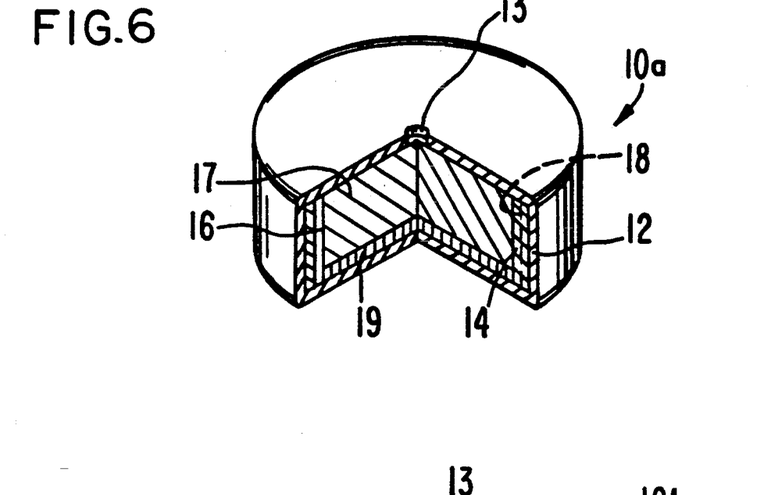
FIG. 6 is an opened view of another embodiment of an osmotic engine according to the present invention.
Figure 7:
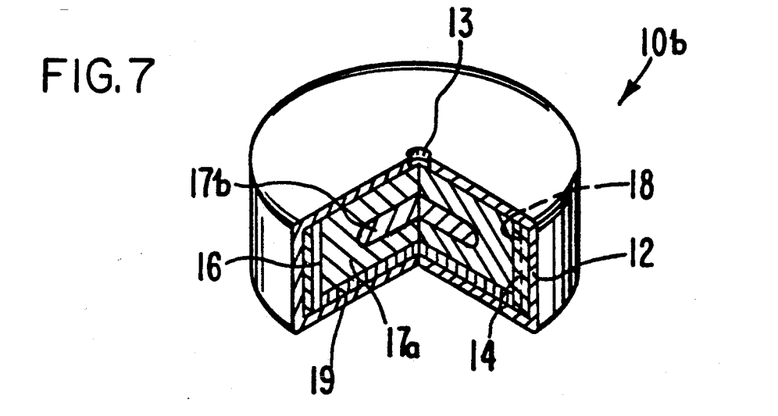
FIG. 7 is an opened view of another embodiment of an osmotic engine according to the present invention.
Figure 8:
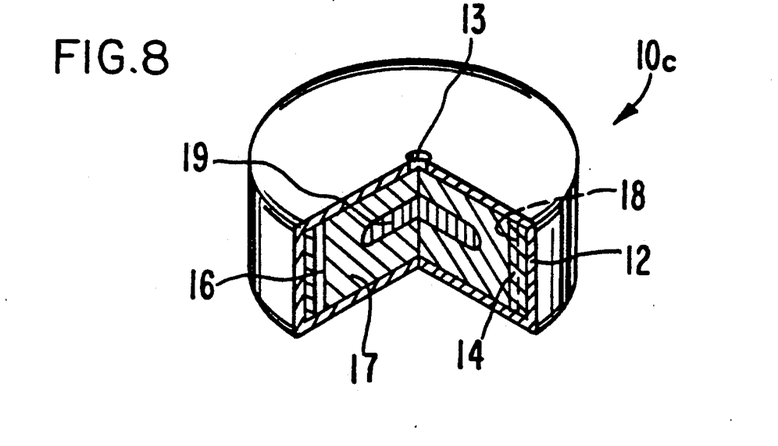
FIG. 8 is an opened view of yet another embodiment of an osmotic engine according to the present invention.

FIGS. 1 and 2 illustrate different embodiments of a new and useful osmotically driven syringe for dispensing a liquid beneficial agent. FIGS. 3–5 illustrate one embodiment of an osmotic engine useful for driving the syringe and FIGS. 6–8 illustrate three alternate embodiments of osmotic engines useful for driving the syringe.

Referring to FIG. 1, syringe 20 comprises a housing 22 with a movable piston 24 therein. The piston 24 separates the interior of housing 22 into an agent compartment 23 and a driving compartment 26. Piston 24 forms a sliding fluid-tight seal with the internal surface of housing 22. Piston 24 may be made of rubber, nylon, polytetrafluoroethylene and the like. Syringe 20 has a delivery port 25 which can be shaped to accept a hypodermic needle, an IV catheter or the like. The syringe housing 22 may be made from well known materials, such as metals or plastics that are inert relative to the liquids they contact and are not irritating to the skin. Examples of such materials are polyolefins such as polypropylene and polyethylene, polyesters, polyamides, polycarbonates, stainless steel and aluminum. Of these, polypropylene is preferred.

When Syringe 20 is used as a portable infusion pump located outside an animal body, a container 30 of a suitable fluid for driving the osmotic engine 10 is preferably used. As illustrated in FIG. 1, container 30, holding a liquid 40, is attached to the end portion 28 of syringe 20 using suitable fastening means, such as screw threads (not shown in the figure). Container 30 has an annular shoulder 35, so that when container 30 is attached to syringe 20, the osmotic engine 10 is tightly compressed between shoulders 27 and 35 with the passageway 13 providing a fluid flow path between the interior of engine 10 and the driving compartment 26. Preferably, the shoulders 27 and 35 provide a fluid-tight seal with the osmotic engine 10 to prevent leakage of the driving fluid from the pressurized driving compartment 26 into container 30. Container 30 preferably contains a wicking material 41 such as a sponge or a hydrogel material. The wicking material 41 maintains the wall 12 of engine 10 continuously wet regardless of the movement or physical orientation of the syringe and container assembly.

Alternatively, the osmotically driven syringe may be used in an aqueous environment (e.g., implanted within an animal body) in which case the container 30 and the reservoir 40 are not needed. FIG. 2 illustrates an osmotically driven syringe 60 which is adapted to be used in an aqueous environment. Unlike syringe 20 (FIG. 1), syringe 60 has no container 30 holding a reservoir of a liquid. Instead, the osmotic engine 10 is attached to the end of syringe 60 with the bottom surface 11 (e.g., the surface opposite orifice 13) of osmotic engine 10 exposed to the external aqueous environment. Engine 10 is attached to syringe 60 using suitable fastening means which tightly compress engine 10 between shoulders 27 and 35. Preferably, shoulders 27 and 35 provide a fluid tight seal against the osmotic engine 10.

In operation, syringes 20 and 60 may be filled with a suitable beneficial agent by injecting the beneficial agent through a fluid injection port 21. Injection port 21 has a rubber septum sealing the opening. A hypodermic needle can be inserted through the rubber septum in order to inject a liquid beneficial agent into compartment 23. Agents that can be dispensed by syringes 20 and 60 include drugs, antibacterials, antifungals, plant growth promoters, surfactants, chemical reactants, and the like. It is within the scope of the present invention to utilize a syringe 20 or 60 which has been prefilled with a dose of a liquid beneficial agent or which is filled by the patient, a nurse or a physician immediately before use.

Those skilled in the art will of course appreciate that in cases where it is desirable to have the syringe 20 or 60 begin immediately dispensing the beneficial agent, the piston 24 is preferably positioned immediately adjacent the osmotic engine 10 in order to minimize the volume of compartment 26 and thereby minimize the time required for the osmotic engine 10 to fill compartment 26 with pumped solution and begin pumping the beneficial agent from compartment 23. Alternatively, compartment 26 may be filled with a liquid before installing engine 10 in order to minimize engine startup time. Next, the osmotic engine 10 is placed within the enlarged end portion 28 of syringe 20 or 60. It is important to orient osmotic engine 10 with the delivery orifice 13 facing piston 24. Then, the housing 30 (as shown in FIG. 1), or the end cap 29 (as shown in FIG. 2), is connected, such as by screwing or snapping, to the enlarged portion 27, 28, thereby tightly securing the osmotic engine 10, in fluid sealing fashion, between annular shoulders 27 and 35.

After attaching the container 30 to syringe 20, a liquid 40 is introduced into container 30 through port 33. Preferably, the liquid comprises sterile water but other liquids can also be used. Ambient pressure is maintained within container 30 by means of a vent 34 that extends through the wall of container 30. The vent 34 is filled with a material that is permeable to air but not permeable to the liquid.

The assembled syringe 20 can be strapped or otherwise secured to the patient with a catheter running from delivery port 25 to a needle (not shown) penetrating the skin. Alternatively, the needle can be inserted into a vein and the syringe utilized as an IV infusion device. When the osmotically driven syringe is used in combination with a subcutaneous or IV needle, the needle is preferably composed of stainless steel and has a gauge in the range of about 25 to 30.

In operation the liquid 40 permeates through surface 11 of semipermeable wall 12 into osmotic engine 10 where it forms a solution of the osmotic solute 17. The solution is pumped from the osmotic engine 10 into compartment 26. After compartment 26 is filled, the pumping of solution from osmotic engine 10 causes piston 24 to move toward delivery port 25, thereby delivering the beneficial agent from compartment 23 through port 25.

When using syringe 60, the syringe is simply placed with surface 11 of osmotic engine 10 exposed to a liquid, preferably aqueous liquid, environment. The liquid permeates through wall 12 and engine 10 pumps driving fluid in the same way as described above in connection with syringe 20.

An important feature of the present invention is the ability to deliver a beneficial agent, such as a drug, at a pre-determined non-constant drug delivery rate profile in order to optimize the treatment of a patient. The selection and distribution of the materials within osmotic engine 10 will determine the drug delivery rate profile for the syringe. FIGS. 3-8 illustrate several examples of osmotic engines which, in conjunction with syringe 20 or syringe 60, can deliver a beneficial agent at selected delivery rate profiles. However, the present invention is not limited to the illustrated embodiments and those skilled in the art will recognize that numerous variations in the delivery rate profile may be achieved utilizing the teachings contained herein.

A first embodiment of the osmotic dispensing device comprises a syringe of the type illustrated in FIG. 1 or 2, having an osmotic engine 10 of the type illustrated in FIGS. 3-5. Osmotic engine 10 is comprised of a shaped semipermeable or microporous wall 12 surrounding a tablet 16 of an osmotic solute represented by 17. A delivery orifice 13 through semipermeable wall 12 provides access to the interior of osmotic engine 10. Wall 12 is permeable to an external liquid (i.e., the liquid in container 30) and has a sufficient degree of impermeability to solute 17 within engine 10 to generate an osmotic pressure differential across wall 12 after exposure of wall 12 to the external liquid. When osmotic engine 10 is exposed to a liquid, such as water, the liquid permeates through wall 12 and forms a solution of the solute 17. As fresh liquid continues to permeate through wall 12, the solution of solute 17 which forms within engine 10 is pumped through passageway 13. Thus, when osmotic engine 10 is secured within end portion 28 of syringe 20 or 60, the solution pumped through passageway 13 enters driving compartment 26, eventually moving piston 24 to deliver the beneficial agent 23.

Preferably, a grooved ring 14 is provided within engine 10. The ring 14 is made of a rigid, non-dissolving material such as rigid plastics, ceramics, glasses and/or metals. In order for the osmotic engine 10 to have sufficient strength and rigidity to be used as an osmotic driver in an osmotically driven syringe according to the present invention, the ring 14 is preferably comprised of a material having a Youngs modulus of at least about 50,000 psi and a compressive strength at 10% compression of at least about 20,000 psi. Most preferably, the ring 14 is comprised of an acetyl resin or similar material. As best shown in FIGS. 4 and 5, the inner surface of ring 14 is provided with a plurality of longitudinally extending grooves 18. The ring 14 may be formed, for example, by conventional machining or molding techniques.

Because ring 14 is composed of a rigid non-dissolving material, its structural integrity is not affected by the pumping of solution through osmotic engine 10. As the solute 17 within osmotic engine 10 is dissolved, the ring 14 provides a rigid structural support for the semipermeable wall 12. Thus, as the solution of solute 17 is delivered, the osmotic engine 10 retains its original shape and strength, (e.g., a compressive pressure of more than 20,000 psi is necessary to collapse the osmotic engine 10) even after substantially all of the solute 17 has been pumped therefrom).

The longitudinally extending grooves 18 in the ring 14 provide a further advantage. Each of the grooves 18 provides an open passageway between ring 14 and the outer circumferential surface of tablet 16 for conveying the liquid solution pumped through osmotic engine 10. In prior art engines, the entire volume within the semipermeable outer wall of the osmotic engine was typically occupied with the osmotically active solute or other solid material. Before these prior art osmotic engines could begin pumping solution, the imbibed liquid had to first dissolve enough of the solute to open a flow path through and/or around the solute tablet. This created an initial delay between the time when the liquid begins to permeate through the membrane wall of the osmotic engine and the time when the osmotic engine begins pumping solution out of the delivery passageway.

The open grooves 18 in ring 14 greatly reduces the initial delay period. Since the grooves 18 are initially open (see FIG. 5), the imbibed liquid need not dissolve a fluid flow path through or around the entire tablet 16 before the solution can reach the passageway 13. Therefore, ring 14 with open grooves 18 greatly shortens the time required for osmotic engine 10 to begin pumping solution.

The osmotic engine 10 is made by first forming a tablet 16 of a solid solute material using a conventional tablet forming press. The formed tablet 16 is then inserted into the center of ring 14. The ring 14, with tablet 16 pressed therein, is then coated with a solution of a suitable semipermeable film forming material in accordance with known methods to form the semipermeable/microporous wall 12. Lastly, the passageway 13 is drilled into one side of osmotic engine 10 using a drill, laser, punch, die cutter or other known orifice forming technique. The osmotic engine 10 may optionally have more than one delivery orifice 13. The maximum and minimum dimensions for passageway 13 are known in the art. Other standard manufacturing procedures are described in *Modern Plastics Encyclopedia*, Vol, 46, pages 62 to 70, 1969; in *Remington's Pharmaceutical Science*, Fourteenth Edition, pages 1649 to 1968, 1970, published by Mack Publishing Co., Easton, Pa.; in *The Theory and Practice of Industrial Pharmacy*, by Lachman, et al, pages 197 to 225, 1970, published by Lea & Febiger, Philadelphia, Pa.; and in U.S. Pat. No. 3,845,770.

In the first embodiment of osmotic engine 10 shown in FIGS. 3-5, tablet 16 contains only a fraction of the minimum amount of solute 17 necessary to drive engine 10 at a constant delivery rate for a period of time necessary to deliver all of the beneficial agent at that rate. In operation, liquid (e.g., liquid 40) permeates through wall 12 where it forms a saturated solution of osmotic solute 17. The liquid is imbibed through wall 12, and the saturated solution is pumped through passageway 13, at a first rate which is determined by the osmotic imbalance between the saturated solution and the external liquid. As the osmotic engine 10 pumps saturated solution of solute 17 into driving compartment 26 at the first rate, piston 24 is forced to slide forward in housing 22 and deliver beneficial agent from compartment 23. Because the driving fluid (i.e., the saturated solution) is a liquid and therefore substantially incompressible, the beneficial agent is delivered from compartment 23 at substantially the same rate at which the saturated solution is pumped from engine 10, e.g., at the first rate.

After engine 10 has pumped saturated solution for some period of time, the amount of osmotic solute 17 in engine 10 becomes depleted and the concentration of the solution formed in engine 10 falls below saturation. Thereafter, the external liquid permeates through wall 12, and forms a subsaturated solution of solute 17 which is pumped through passageway 13, at a second rate which is less than the first rate. Unlike the first rate which was substantially constant, the second rate is variable and gradually decreases with time. As the osmotic engine 10 pumps the now subsaturated driving fluid through passageway 13 into compartment 26 at the second rate, piston 24 is forced to slide forward in housing 22 and deliver beneficial agent from compartment 23. Because the pumped solution is substantially incompressible, the beneficial agent is delivered from compartment 23 at substantially the same rate at which subsaturated solution is pumped from engine 10, e.g., at the second rate.

Figure 9:
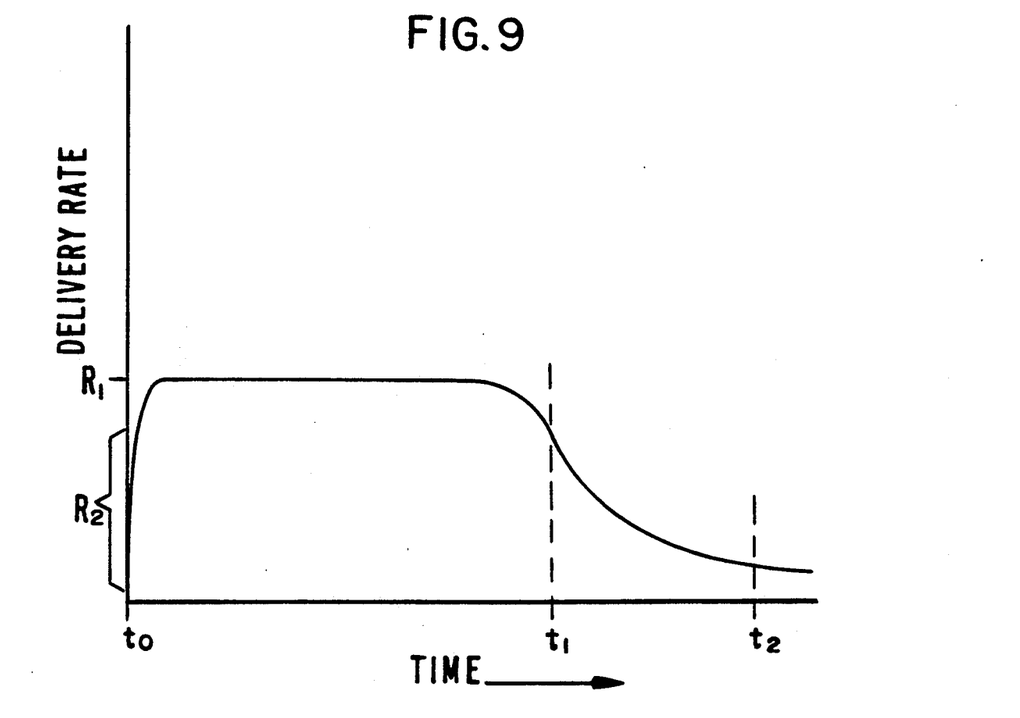
FIG. 9 is a graph showing the volumetric delivery rate of a beneficial agent from an osmotically driven syringe over time, the syringe utilizing the osmotic engine illustrated in FIG. 4.

A typical delivery rate profile for a syringe 20 or 60, having the osmotic engine 10 of FIGS. 3-5, is shown in FIG. 9. The syringe is placed in operation by exposing the semipermeable wall 12 to an external liquid, such as liquid 40 in a container 30. The volumetric delivery rate of the syringe quickly rises during the initial start-up phase. After the initial start-up phase, the syringe delivers beneficial agent at a first delivery rate $R_1$ as indicated by the substantially horizontal portion of the curve. Thus, over the time period $t_0$ to $t_1$, the syringe delivers beneficial agent at a substantially constant rate $R_1$. At about time $t_1$, the osmotic engine 10 begins pumping a subsaturated solution of osmotic solute 17. Thus, after time $t_1$, the concentration of the solution of solute 17 formed within osmotic engine 10 gradually decreases towards zero. Likewise, the pumping rate of osmotic engine 10 decreases with time after time $t_1$. As a result, the syringe delivers beneficial agent over the time period $t_1$ to $t_2$ at a gradually declining delivery rate, $R_2$.

The osmotically driven syringes of the prior art utilize osmotic engines which are designed to deliver substantially all of the beneficial agent dose during the period of time when the osmotic engine pumps saturated solution, i.e., during time period $t_0$ to $t_1$. Unlike the prior art devices, the first embodiment of the osmotically driven dispenser is purposefully designed to deliver beneficial agent over a period of time greater than the time period during which engine 10 pumps saturated driving fluid, i.e., $t_0$ to $t_1$. Thus, the syringe delivers beneficial agent at a first rate $R_1$ over the time period $t_0$ to $t_1$, following which, the syringe delivers beneficial agent over the time period $t_1$ to $t_2$ at a gradually declining delivery rate $R_2$ which is less than the first delivery rate $R_1$. In order to insure that the osmotic engine 10 pumps saturated solution for only a portion of the drug delivery period (i.e., for only a portion of the time period from $t_0$ to $t_2$), the total volume of saturated solution pumped by engine 10 must be less than the volume of beneficial agent in compartment 23 of the syringe. Mathematically, this may be expressed as follows:

$$\int_{t_0}^{t_1} R dt < V$$

wherein:
  R is the volumetric pumping rate of osmotic engine 10;
  $t_0$ is the time at which osmotic engine 10 begins pumping (initially saturated) solution;
  $t_1$ is the time at which osmotic engine 10 begins pumping subsaturated solution; and
  V is the volume of beneficial agent in compartment 23 of the syringe.

The integral may be calculated experimentally by plotting the volumetric pumping rate of osmotic engine 10 as a function of time with frequent measurement of the concentration of the solution being pumped in order to determine the time at which osmotic engine 10 stops pumping saturated solution and begins pumping subsaturated solution. The integral is then calculated by measuring the area under the curve between time $t_0$ and time $t_1$.

A second embodiment of the osmotically driven dispenser comprises a syringe of the type illustrated in FIG. 1 or 2 having an osmotic engine 10a of the type illustrated in FIG. 6. This second embodiment utilizes an osmotic engine 10a having a bilayered tablet 16 comprising a layer of a gas generating means 19, preferably an effervescent couple, and a layer of an osmotic solute 17. As liquid permeates through wall 12, it wets the gas generating means 19 which reacts to form a gas. The means 19 comprises a material which, when wetted by the external liquid, reacts to form a gas such as carbon dioxide. The gas generating means 19 suitable for the purpose of the invention is, in a presently preferred embodiment, an effervescent couple or composition. Generally, the gas generating means 19 when comprised of an effervescent couple will include at least one osmotically effective compound, for example, sodium bicarbonate, which itself exhibits an osmotic pressure gradient. In those applications when the gas generating means exhibits a limited osmotic pressure gradient, an osmotically effective compound may be homogeneously or heterogeneously mixed with the layer of the gas generating means 19 in the osmotic engine 10. In operation, these compounds attract fluid into the engine 10, wetting the gas generating means 19 and causing the materials of the couple to react and effervesce (e.g., produce a gas). The gas which is produced is pumped out of engine 10, pressurizes compartment 26 and displaces piston 24. Alternatively, the means 19 may comprise an agent which reacts directly with the imbibed liquid to form a gas. The gas generated during the reaction flows along open grooves 18 and passes through passageway 13, thereby pressurizing driving compartment 26. The increased pressure exerted on piston 24 forces it to move forward in housing 22 which causes the syringe to deliver beneficial agent through delivery port 25 at a first rate $R_1$. Typically, the means 19 reacts quickly upon exposure to the imbibed liquid to form a gas. Thus, the layer of gas generating means 19 may be beneficially used to provide an initial pulse of a beneficial agent to a patient.

The osmotic engine 10a can be manufactured by standard techniques. For example, separate layers of the osmotic solute 17 and the solid gas generating means 19 are pressed, using convention bilayer tableting equipment, into a solid tablet 16 having a size suitable for insertion into ring 14.

Figure 10:
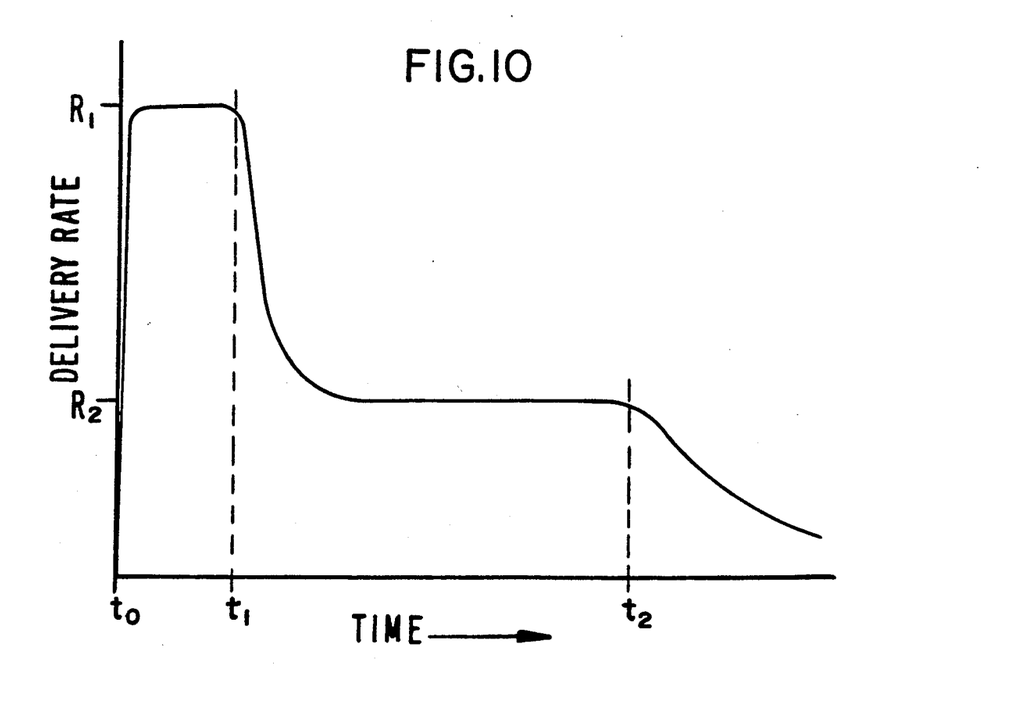
FIG. 10 is a graph showing the volumetric delivery rate of a beneficial agent from an osmotically driven syringe over time, the syringe utilizing the osmotic engine illustrated in FIG. 6.

A typical delivery profile for an osmotically driven syringe utilizing the osmotic engine 10a of FIG. 6 is shown in FIG. 10. After the engine 10a is exposed to an external liquid, the gas generating means 19 becomes wetted by the imbibed liquid, causing the gas generating reaction to start. After the initial start-up phase when the delivery rate of the syringe quickly increases from zero, the syringe begins to deliver beneficial agent at a high first rate $R_1$. The syringe delivers beneficial agent at rate $R_1$ during the time period from $t_0$ to $t_1$, during which time period the gas generating reaction is taking place. During the gas generating reaction, the layer of osmotic solute 17 remains substantially intact within the osmotic engine 10a. However, as the means 19 is consumed by the gas generating reaction, the external liquid which permeates through wall 12 begins to dissolve solute 17 and forms a solution of solute 17 within engine 10a. As fresh external liquid permeates through wall 12, by the osmotic imbalance between the solute 17 and the external liquid, the solution within engine 10a is pumped through passageway 13 into driving compartment 26 at a second rate, $R_2$. After the gas generating reaction is completed (i.e., after time $t_1$) the delivery rate falls to the lower rate $R_2$ which is determined by the rate of pumping of solution (of solute 17) from engine 10a. The syringe then continues to deliver beneficial agent at a substantially lower delivery rate, $R_2$. During the time period from $t_1$ to $t_2$, the syringe is driven primarily by the pumping of osmotic solute 17 from osmotic engine 10a. In this embodiment, the second rate $R_2$ (which is solution driven) is much lower than the first rate $R_1$ (which is gas driven). If the solution formed in engine 10a is saturated, the engine will pump solution into compartment 26 at a substantially constant rate as long as the solution formed within engine 10a remains saturated.

The delivery rate profile of FIG. 10 is particularly useful in instances where it is desirable to quickly establish a particular blood plasma concentration of beneficial agent in a patient in order to obtain a beneficial pharmacological response. The gas generating reaction provides an initial pulse in the delivery rate of the beneficial agent to quickly achieve the desired blood plasma concentration level. The length of the pulse (i.e., the length of time from $t_0$ to $t_1$) may be adjusted by varying the amount of gas generating means 19 provided in engine 10a. The delivery rate $R_1$ may be adjusted by the choice of the gas generating means 19 provided in engine 10a. For instance, if a relatively high initial delivery rate $R_1$ is desired, a gas generating means is chosen which generates a relatively large volume of gas upon exposure to the imbibed external liquid, e.g., a mixture of sodium bicarbonate and an acidic material. If it is desirable to deliver agent at an initial delivery rate $R_1$ for only a short period of time, the amount of gas generating means in engine 10 may be appropriately limited. Following the initial pulse, the second delivery rate $R_2$ can be targeted for example to a level suitable for maintaining a desired blood plasma concentration of the beneficial agent.

A third embodiment of the osmotically driven dispenser comprises a syringe of the type illustrated in FIG. 1 or 2 having an osmotic engine 10b of the type illustrated in FIG. 7. The osmotic engine 10b has a tablet 16 composed of different materials, including a layer of a gas generating means 19, and a layer containing two different osmotic solutes 17a and 17b. Osmotic solutes 17a and 17b have differing degrees of solubility in the liquid permeating through wall 12. The layer of gas generating means 19 operates in the same manner as described above in connection with the FIG. 6 embodiment. The means 19 is activated by an external liquid (e.g., liquid 40) permeating through wall 12, causing a gas generating reaction to occur. The gas generating reaction pressurizes compartment 26 causing piston 24 to slide forward in housing 22, thus causing the syringe to deliver beneficial agent from compartment 23 at a first rate $R_1$ for a period of time from $t_0$ to $t_1$.

After the gas generating reaction is substantially complete, liquid continues to permeate through wall 12 by the osmotic imbalance caused between one of the two solutes 17a and 17b and the external liquid. Because of their differing solubilities, solutes 17a and 17b cause engine 10b to pump at different sequential pumping rates $R_2$ and $R_3$, respectively. Because solute 17a completely surrounds and encapsulates solute 17b, solute 17a will control the rate of pumping ($R_2$) immediately following the gas driven pumping ($R_1$). In the illustrated embodiment, solute 17a has greater solubility in the liquid than does solute 17b, and accordingly, generates a greater osmotic pressure than does solute 17b. Thus, solute 17a will cause liquid to permeate through wall 12 at a higher rate than the rate at which liquid permeates through wall 12 by solute 17b, i.e., $R_2$ is greater than $R_3$.

Figure 11:
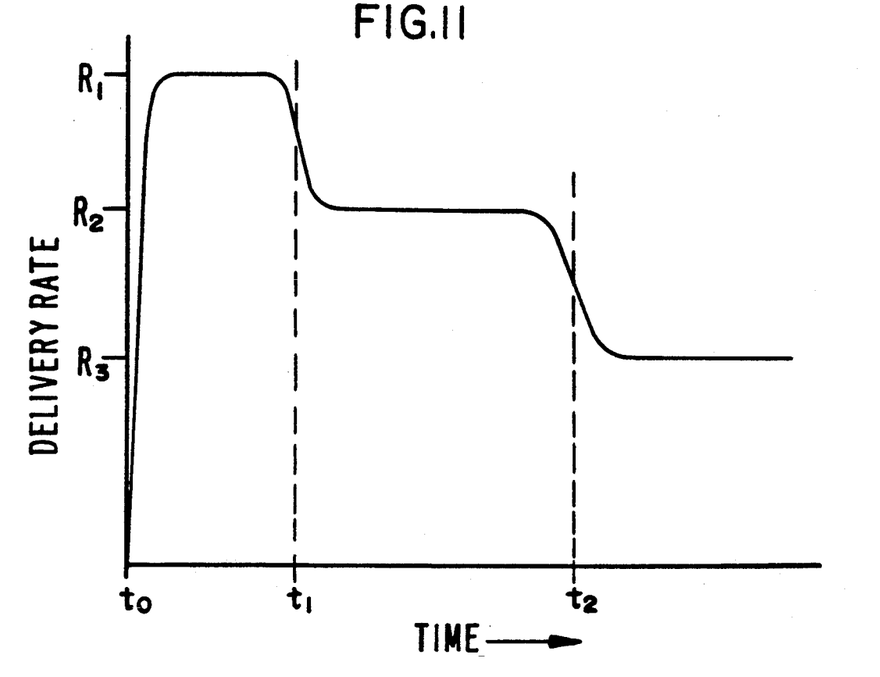
FIG. 11 is a graph showing the volumetric delivery rate of a beneficial agent from an osmotically driven syringe over time, the syringe using the osmotic engine illustrated in FIG. 7.

FIG. 11 illustrates the beneficial agent delivery profile of an osmotically driven syringe utilizing the osmotic engine 10b of FIG. 7. The delivery profile includes a high initial delivery rate $R_1$ which is driven by the gas generating means 19 and which continues for a predetermined period of time from $t_0$ to $t_1$, immediately followed by a medium agent delivery rate $R_2$ which is driven by the solute 17a and which continues for a predetermined period of time from $t_1$ to $t_2$, which is in turn followed by a low agent delivery rate $R_3$ which is driven by the solute 17b and which continues for a predetermined period of time after $t_2$. Those skilled in the art will appreciate that the delivery rate profile illustrated in FIG. 11 can be used to great advantage for delivering drugs which have the greatest beneficial impact when given in a variable rate of delivery. For example, certain diet medications have greatest impact when administered at relatively high delivery rates just prior to scheduled meal times. Other medications may be beneficially delivered at higher rates during certain hours of the day to match the circadian cycles of the patient. Those skilled in the art will appreciate that any number of delivery profiles may be configured to meet the needs of a particular patient or a particular beneficial agent.

A fourth embodiment of the osmotically driven dispenser comprises a syringe of the type illustrated in FIG. 1 or 2 having an osmotic engine 10c of the type illustrated in FIG. 8. Osmotic engine 10c contains a tablet 16 composed of an inner layer of a gas generating means 19 which is surrounded by an osmotic solute 17. The configuration of tablet 16 shown in FIG. 8 may be made for example by first compressing a tablet of materials forming an effervescent couple. Then the compressed effervescent couple materials are coated with osmotic solute 17 using known coating or dry tableting techniques. The tablet 16 is then inserted into ring 14. Lastly, wall 12 and passageway 13 are formed as described earlier.

Figure 12:
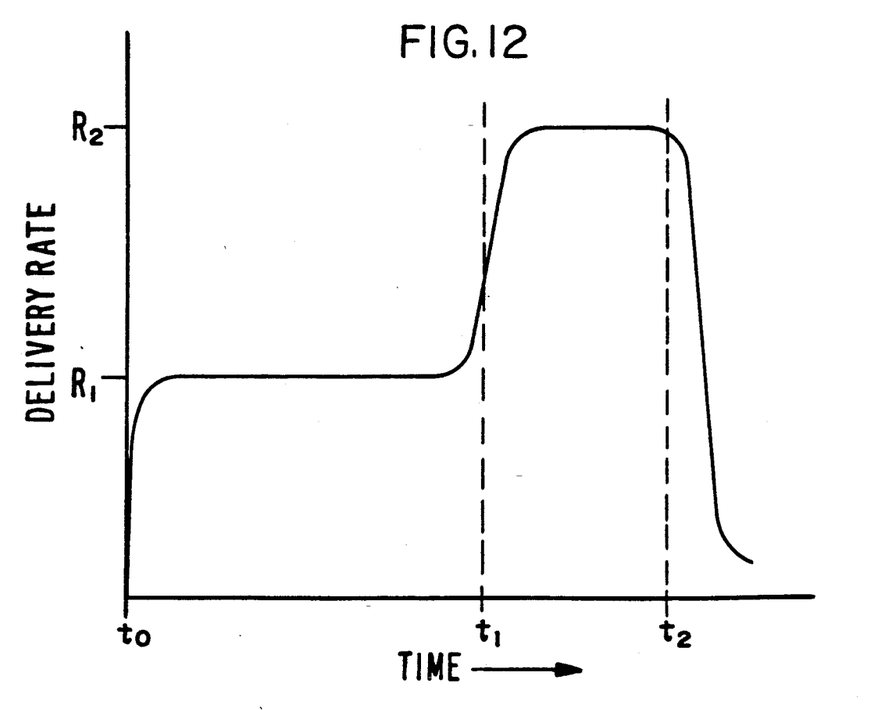
FIG. 12 is a graph showing the volumetric delivery rate of a beneficial agent from an osmotically driven syringe over time, the syringe utilizing the osmotic engine illustrated in FIG. 8.

The drug delivery profile for an osmotically driven syringe utilizing the osmotic engine 10c of FIG. 8 is shown in FIG. 12. The delivery profile proceeds at a low first delivery rate $R_1$ from $t_0$ to $t_1$. After time $t_1$, the gas generating reaction takes place causing a pulse in the delivery rate profile from time $t_1$ to $t_2$, during which time the agent is delivered at a higher rate $R_2$.

Wall 12 of osmotic engine 10 is comprised, in total or at least in part, of a membrane that possesses permeability to an external liquid such as water while simultaneously being substantially impermeable to osmotic solute 17 and the gas generated by the gas generating means 19. Typical materials for forming wall 12 include synthetic or naturally occurring semipermeable and/or microporous membranes known to the art as osmosis and reverse osmosis membranes. Preferably, wall 12 is comprised of a cellulose ester. Examples of suitable membrane materials include commercially available unplasticized cellulose acetate, plasticized cellulose acetate, reinforced cellulose acetate, cellulose nitrate with 11% nitrogen, cellulose diacetate, cellulose triacetate, agar acetate, amylose triacetate, beta glucan acetate, beta glucan triacetate, cellulose acetate, acetaldehyde dimethyl acetate, cellulose acetate ethyl carbamate, cellulose acetate phthalate, cellulose acetate methyl carbamate, cellulose acetate succinate, cellulose acetate dimethaminoacetate, cellulose acetate ethyl carbonate, cellulose acetate chloroacetate, cellulose acetate ethyl oxalate, cellulose acetate methyl sulfonate, cellulose acetate butyl sulfonate, cellulose acetate propionate, cellulose acetate p-toluene sulfonate, triacetate of locust gum bean, cellulose acetate with acetylated hydroxyethyl cellulose, hydroxylated ethylene-vinylacetate, cellulose acetate butyrate having a viscosity of from about 10 seconds to about 50 seconds, cellulose acetate butyrate containing about 17 percent of combined butyryl and about 29.5 percent acetyl, cellulose acylate, cellulose diacylate, cellulose triacylate, permselective, aromatic nitrogen-containing polymeric membranes that exhibit water permeability and essentially no solute passage, osmosis membranes made from polymeric epoxides, osmosis membranes made from copolymers of an alkylene oxide and alkyl glycidyl ether, semipermeable polyurethanes, semipermeable polyglycolic or polylactic acid and derivatives thereof, thin film membranes as disclosed by Loeb and Sourirajan in U.S. Pat. No. 3,133,132, the membranes of ionically associated polyelectrolytes, the polymers formed by the coprecipitation of polycation and a polyanion as described in U.S. Pat. Nos. 3,276,586; 3,541,005; 3,541,006; 3,546,142; 3,173,876; derivatives of polystyrene such as poly(sodium styrenesulfonate) and poly(vinylbenzyltrimethyl-ammonium chloride), and the like. Generally, membranes having an osmotic fluid permeability of $10^{-5}$ to $10^{-9}$ cm$^3$/atm/hr against a saturated solute solution at the temperature of use while simultaneously possessing a sufficient degree of impermeability to the solute to generate an osmotic pressure differential across the membrane are useful and within the spirit of the invention.

Osmotically active compounds useful as the osmotic solute 17 include compounds such as magnesium sulfate, magnesium chloride, sodium chloride, lithium chloride, potassium chloride, potassium sulfate, sodium carbonate, sodium sulfite, lithium sulfate, sodium bicarbonate, potassium bicarbonate, calcium bicarbonate, sodium sulfate, calcium sulfate, potassium acid phosphate, calcium lactate, magnesium succinate, citric acid, succinic acid, tartaric acid, soluble carbohydrates such as raffinose, glucose, lactose, fructose, mannitol, and sorbitol, and mixtures thereof and the like. Of these, sodium chloride, potassium chloride, glucose and lactose are preferred. The osmotically active solute may also be comprised of a water soluble polymer. The solid solute can be in any suitable physical form such as particles, crystals, pellets, tablets, strips, film, granules and the like.

In syringes that are to be used to administer a drug intravenously, the osmotic pressure of the solute solution must exceed the blood pressure of the animal (about 10 kPa in humans). The osmotic pressure of sodium chloride is sufficiently high to overcome the blood pressure of an animal.

The preferred gas generating means 19 comprises an effervescent couple including at least one preferably solid acidic material and a preferably solid basic material that dissolve and react in an aqueous fluid that enters the device to produce carbon dioxide effervescence that leads to an increased pressure in the driving compartment 26 which forces piston 24 to slide forward in housing 22 resulting in displacement of beneficial agent from compartment 23. The acids that can be used include pharmaceutically acceptable organic acids such as malic, fumaric, tartaric, itaconic, maleic, citric, adipic, succinic and mesaconic, mixtures thereof, and the corresponding anhydride such as itaconic anhydride and citriconic anhydride. Also, inorganic acids can be used such as sulfamic or phosphoric, and the acid disclosed in U.S. Pat. No. 3,325,357. Acid salts such as the salts of organic food can be used including monosodium citrate, potassium acid tartrate and potassium bitartrate. The basic compounds include preferably the pharmaceutically acceptable metal carbonate and bicarbonate salts such as alkali metal carbonates and bicarbonates or alkaline earth carbonates and bicarbonates and mixtures thereof. Exemplary materials include the alkali metal compounds, lithium, sodium, and potassium carbonate and bicarbonate, and the alkaline earth compounds magnesium and calcium carbonate or bicarbonate. Also useful are ammonium carbonate, ammonium bicarbonate, and ammonium sesquecarbonate. The combination of certain of these acids and bases results in a more rapid gas production or effervescence when contacted by water than do other of the above-listed groups. In particular, either citric acid or a mixture of citric acid and tartaric acid and sodium bicarbonate give a rapid gaseous reaction that is useful for quick release from the device. It will be understood the amount of acidic and basic materials in a couple can vary over a wide range to satisfy the amount of effervescence needed to dispense an agent. The essentially anhydrous or dry couple is preferably substantially stoichiometrically balanced to produce a combination that generates carbon dioxide. Also, the acid and base materials can be used in any convenient proportion between 1 to 200 parts and 200 to 1 parts on a weight basis to produce the desired results.

Additionally, the gas generating means 19 includes effervescent couples which form a salt and can hydrate and store up to several moles of water per mole of salt. For these couples, the rate at which gas is produced and agent dispensed from the device is controlled by the influx of water imbibed into the system. Control is effected by hydration of the salt that quenches the chain reaction of gas production caused by the acid base reaction. Further, a water scavenging process can be added to the compartment to fulfill the same function. The gas generating means 19 can also comprise a single gas producing agent, such as calcium carbide, that evolves a gas on exposure to water. The latter means is particularly useful for non-therapeutic applications or where the device is used as a displacement pump. In this embodiment the fluid in compartment 23 is inert (e.g., water) and the syringe 20 or 60 is interconnected by well known means to a reservoir of a fluid beneficial agent to be discharged, such that the inert fluid displaces the beneficial agent from the reservoir in a predetermined regimen to the desired administration site.

Most preferably, the gas generating means 19 includes a foaming agent, such as a surfactant, having suitable foaming properties to stabilize the gas generated in the osmotic engine 10. The surfactant when mixed with the imbibed external fluid and the gas produced by the effervescent couple, forms a foam. The foam serves to give "body" to the gas phase and helps prevent the gas from leaking past the piston 24 into the chamber containing the beneficial agent 23. The surfactant can be cationic, anionic or nonionic. Exemplary cationic surfactants include, lauryldimethylbenzylammonium chloride p-diisobutylphenoxyethoxyethyl-dimethylbenzylammonium chloride, alkyldimethylbenzylammonium chloride, laurylisoquinolinium bromide, cetylethyldimethylammonium bromide, stearyl-dimethylbenzylammonium chloride, N-soya-N-ethyl-morpholinium-ethosulphate, N(acyl-colaminoformyl-methyl)pyridinium chloride, a mixture comprising alkyl ($C_9H_{19}$ to $C_{15}H_{31}$) tolylmethyltrimethylammonium chloride and lauryl-isoquinolinium bromide, cocoamidoalkyl betaine, and N-lauryl-myristyl-$\beta$-aminopropionic acid. Exemplary anionic surfactants include linear alkylaryl sulfonates prepared by Friedel-Crafts reaction of an olefin and benzene wherein the olefin has from 10 to 18 carbon atoms, and the alkali metal salts thereof, and other anionic surfactants such as alkylaryl sulphonate, capryl imidazoline derivatives, dioctylester of sodium sulphosuccinic acid, sodium lauryl sulfate, sodium salt of alkylated aryl polyether sulphate, triethanolamine salt of lauryl sulphate, tripthanolamine salt of alkylaryl sulfonate, and mixtures thereof. Exemplary nonionic surfactants include alkylated aryl polyether alcohol, polyethylene glycol tertdodecyl thioether, fatty acid amide condensates, aromatic polyglycol ether condensates, secondary amide of lauric acid, fatty acid alkanolamine condensates, sorbitan monolaurate, sorbitan monolaurate polyoxyethylene, sorbitan mono-oleate, sorbitan mono-oleate polyoxyethylene derivative, mannide mono-oleate polyoxyethylene lauryl ether, polyoxyethylene esters of mixed resins and fatty acids, and mixtures thereof, and surfactants generically including the condensation product of a linear aliphatic alcohol having from 8 to 22 carbon atoms in its aliphatic portion and an alkylene oxide wherein the oxide constitutes from about 55 to 80% by weight of the surfactant molecule. The amount of surface active agent used is an amount sufficient to achieve the intended result, normally, the amount will range from 0.01% to about 15% by weight, based on the total weight of all the compounds in the osmotic engine 10. The surface active agents are commercially available and they are also known in *Solubilization By Surface-Active Agents*, by Elworthy, P. H., et al, 1968, published by Chapman and Hall Ltd., London; *Systemic Analysis of Surface-Active Agents*, by Rosen, Milton J., et al, 1972, published by Wiley-Interscience Inc., Sydney; *Encyclopedia of Polymer Science and Technology*, Vol. 13, pages 477 to 486, 1970, published by John Wiley & Sons Inc., New York; and U.S. Pat. Nos. 2,674,619, 3,340,309, 3,504,041, and 3,796,817.

Suitable foam forming agents which can be mixed with the gas generating means 19 for the above described purpose include those that produce a foam that is stable within a wide range of temperature, that produces a foam that does not collapse in the presence of other compounds, and produces a foam that is pharmaceutically acceptable when the syringe 20 or 60 dispenses a drug to an animal. Exemplary foam-formers are alkyl aryl sulphonates, sodium, ammonium and alkanolamine ether sulphates such as monoethanolamine lauryl ether sulphate and dodecyl benzene sulphonate, a mixture consisting of lauryl-amidopropyl-N-dimethylamino acetic acid and stearylamidopropyl-N-dimethylamino acetic acid, a mixture consisting of monoethanolamine lauryl ether sulphate and methyl cellulose in a weight ratio of 3:1, a foaming surfactant consisting of sodium alkyl benzene sulphonate in combination with lauryl sulphate and sodium lauryl sulphoacetate. The amount of foam-forming agent used usually is about 0.01 to 15% by weight based on the total weight of the compounds in the device. Representative foam-formers and foam systems are described in *The Theory and Practice of Industrial Pharmacy*, by Lachman, L. et al, pages 618 to 621, 1970, published by Lea & Febiger, Philadelphia; and in *Cosmeticology*, by Harry, R. G., pages 243 to 250, 1973, published by Chemical Publishing Co. Inc., New York.

In those embodiments of the osmotic engine which utilize a gas generating means 19, at least a portion of the driving fluid produced by engine 10 for driving piston 24 is a gas. In determining the amount of gas generating means 19 needed within engine 10, the compressibility of the gas produced by the gas generating reaction must be taken into account. In a typical syringe, the pressures generated within driving compartment 26 will be such that the volume of gas produced by the gas generating means 19 will be on the order of about 80 to 90% of the volume of the gas at standard atmospheric pressure. Those skilled in the art will appreciate that the compressibility of the gas produced by the gas generating means 19 is simply compensated for by adding from 10 to 20% more gas generating means than would be required at standard atmospheric pressure.

Agents that can be dispensed by syringe 20 or 60 include algicides, air purifiers, anti-oxidants, biocides, catalysts, chemical reactants, cosmetics, drugs, disinfectants, fungicides, fermentation agents, foods, food supplements, fertility inhibitors, fertility promotors, germicides, herbicides, insecticides, micro-organism attenuators, nutrients, pesticides, plant growth promotors, plant growth inhibitors, preservatives, sex sterilants, sterilization agents, vitamins, and other useful agents that benefit the environment of use. The term drug as used herein includes any physiologically or pharmacologically active substance that produces a localized or systemic effect in an animal. The active agent or drug can include inorganic and organic compounds without limitation, and includes hypnotics, sedatives, psychic energizers, tranquilizers, antidepressants, anticonvulsants, muscle relaxants, antiparkinson agents, analgesics, anti-inflammatory agents, anesthetics, muscle contractants, anti-infectives, anti-microbials, anti-malarials, hormonal agents, sympathomimetics, metabolic aberration correcting agents, diuretics, anti-parasitics, neoplastics, hypoglycemic, nutritional agents; fats, ophthalmic agents, elutrolytes, cardiac and diagnostic agents. Additional agents that can be dispensed by syringe 20 or 60 include anti-cancer drugs such as 5-fluorouracil, 5-fluorouracil deoxyribose, bleomycin sulfate, and adriamycin; polypeptides such as insulin and buserelin, analgesics such as morphine sulfate, hydromorphone HCl, oxymorphone HCl and methadone HCl; anti-psychotics such as dihydroergotamine mesylate and promethazine HCl; anti-asthmatics such as aminophylline and terbutaline sulfate; anti-thrombotic agents such as heparin Na, urokinase and streptokinase; hormones such as corticotropin; anti-nausea agents such as metoclopramide HCl; antibiotics such as polymyxin B and amphotericin B; ion chelating agents such as deferoxamine mesvlate; narcotic antagonists such as naloxone HCl; ritodrine HCl; and narcotic analgesics for long term pain relief. Other drugs which are preferably delivered at varying rates to suit the natural or circadian patterns of the body are likewise suitable for delivery from syringes 20 and 60 utilizing an osmotic engine of the type illustrated in FIGS. 3-8. For example, gastric acid secretions are more pronounced during the evening hours and less pronounced during waking hours. Patients suffering from peptic ulcers, therefore, require increased anti-ulcer medications (e.g., ranitidine) overnight. This can be accomplished using an osmotically driven syringe designed to deliver about 75% of the drug dose over the first 12 hour period and the remaining 25% of the dose over the following 12 hour period, administration to begin in the late afternoon or early evening hours.

The osmotically driven syringes of the present invention may be used to deliver dosages having a fluid volume in a range of about 0.2 to about 20 cm$^3$ over a period of about 0.5 to about 15 days. Syringes having a size suitable for implantation in a human or other animal body typically have a compartment 23 which can hold from about 0.2 to 10 cm$^2$ of a liquid beneficial agent. The osmotic engines useful in the osmotically driven syringes disclosed herein typically deliver from about 0.1 to about 40 cm$^3$/day.

Syringe 20 or 60 can optionally be made as a reusable device. That is, agent compartment 23 can be refilled, osmotic engine 10 can be replaced, with another engine having the same or a different pumping rate profile, and (if a fluid reservoir is used) the container 30 can be refilled with fresh liquid 40.

While certain preferred embodiments of the present have been selected for illustration in the drawings and have been described in detail herein, the illustrated embodiments should not be construed as limiting and those skilled in the art will appreciate that various modifications, changes and additions to the illustrated embodiments may be made without departing from the spirit and scope of the present invention as defined in the appended claims.

We claim:

1. An osmotic engine for driving a device adapted to dispense a beneficial agent, the engine comprising a shaped wall surrounding a means for forming a driving fluid and a passageway through the wall for delivering the driving fluid from the engine, at least a portion of the wall being comprised of a material that is permeable to an external liquid, the wall having a sufficient degree of impermeability to an osmotically active material in the engine to generate an osmotic pressure differential across the wall when the wall is exposed to the external liquid;

wherein the means for forming a driving fluid comprises an osmotic solute which is soluble in the external liquid, whereby the external liquid permeates through the wall portion and forms a saturated solution of the solute, the saturated solution being a first driving fluid which is pumped from the engine and through the passageway at a first rate over a first period of time and subsequently the external liquid permeates through the wall portion and forms a subsaturated solution of the solute, the unsaturated solution being a second driving fluid which is pumped from the engine and through the passageway at a second rate over a second period of time which follows the first period of time, the second rate being unequal to the first rate.

2. The osmotic engine of claim 1, wherein the osmotic solute is present in an amount such that:

$$\int_{t_0}^{t_1} R dt < V$$

wherein:
R is the volumetric pumping rate of the osmotic engine;
$t_0$ is the time at which the osmotic engine begins pumping saturated solution;
$t_1$ is the time at which osmotic engine 10 begins pumping subsaturated solution; and
V is the volume of the beneficial agent to be dispensed by the device.

3. The osmotic engine of claim 2, wherein the external liquid comprises water and the first and second driving fluids comprise aqueous solutions of the osmotic solute.

4. The osmotic engine of claim 2, wherein the first rate is substantially constant over a substantial portion of, the first period of time.

5. The osmotic engine of claim 2, wherein the second rate is variable and decreases over the second period of time.

6. An osmotic engine for driving a device adapted to dispense a beneficial agent, the engine comprising a shaped wall surrounding a means for forming a driving fluid and a passageway through the wall for delivering the driving fluid from the engine, at least a portion of the wall being comprised of a material that is permeable to an external liquid, the wall having a sufficient degree of impermeability to an osmotically active material in the engine to generate an osmotic pressure differential across the wall when the wall is exposed to the external liquid;

wherein the means for forming a driving fluid comprises a bilayered tablet having a layer of a gas generating means and a layer of an osmotic solute which generates no gas, said osmotic solute selected from the group consisting of osmotically active salts, acids and carbohydrates, whereby the external liquid permeates through the wall portion and causes the gas generating means to generate a gas, the gas being a first driving fluid which is pumped from the engine and through the passageway at a first rate over a first period of time and subsequently the external liquid permeates through the wall portion and forms a solution of the solute, the solution being a second driving fluid which is pumped from the engine and through the passageway at a second rate over a second period of time which follows the first period of time, the second rate being unequal to the first rate.

7. The osmotic engine of claim 6, wherein the external liquid comprises water and the second driving fluid comprises an aqueous solution of the osmotic solute.

8. The osmotic engine of claim 6, wherein the gas generating means comprises an effervescent couple.

9. The osmotic engine of claim 6, wherein the gas generating means comprises a solid acidic material and a solid basic material that dissolve in the external liquid and react to form a gas.

10. The osmotic engine of claim 9, wherein the gas produced by the gas generating means is carbon dioxide.

11. The osmotic engine of claim 6, wherein the first rate is higher than the second rate.

12. The osmotic engine of claim 2 or 6, wherein the wall is comprised entirely of a material that is permeable to the external fluid.

13. The osmotic engine of claim 2 or 6, wherein the wall is comprised of a cellulose ester.

14. The osmotic engine of claim 2 or 6, wherein the osmotic solute is selected from the group consisting of sodium chloride, potassium chloride, glucose and lactose.

15. The osmotic engine of claim 2 or 6, including a rigid non-dissolving ring-shaped wall support having a plurality of longitudinally extending grooves providing an open fluid flow path extending from the semipermeable wall portion toward the passageway through the wall.

16. The osmotic engine of claim 6, wherein the layer of the osmotic solute further comprises a first solute and a second solute, said first and second solutes having differing solubilities in the external liquid.

17. An osmotically driven dispensing device for continuously delivering a beneficial agent to an environment of use at a predetermined rate profile, the device comprising:

a) a syringe housing having a movable piston therein, the piston dividing the syringe housing into a beneficial agent-containing compartment and a driving compartment;

b) an osmotic engine adjacent said driving compartment, said osmotic engine comprising a shaped wall surrounding a means for forming a driving fluid including an osmotic solute which is soluble in an external liquid and a passageway through the wall for delivering the driving fluid from the engine into the driving compartment, at least a portion of the wall being comprised of a material that is permeable to the external liquid, the wall having a sufficient degree of impermeability to the osmotic solute to generate an osmotic pressure differential across the wall when the wall is exposed to the external liquid;

whereby the external liquid permeates through the wall portion and forms a saturated solution of the solute, the saturated solution being a first driving fluid which is pumped into the driving compartment and thereby drives the piston to deliver beneficial agent from the beneficial agent-containing compartment to the environment of use at a first rate over a first period of time and subsequently the external liquid permeates through the wall portion and forms a subsaturated solution of the solute, the subsaturated solution being a second driving fluid which is pumped into the driving compartment at a second rate over a second period of time which follows the first period of time, the second rate being unequal to the first rate.

18. The device of claim 17, wherein the osmotic solute is present in an amount such that:

$$\int_{t_0}^{t_1} R\,dt < V$$

wherein:
  R is the volumetric pumping rate of the osmotic engine;
  $t_0$ is the time at which the osmotic engine begins pumping saturated solution;
  $t_1$ is the time at which osmotic engine 10 begins pumping subsaturated solution; and
  V is the volume of the beneficial agent to be dispensed.

19. The device of claim 18, wherein the external liquid comprises water and the driving fluid comprises an aqueous solution of the osmotic solute.

20. The device of claim 18, wherein the first rate is substantially constant over a substantial portion of the first period of time.

21. The device of claim 18, wherein the second rate is variable and decreases over the second period of time.

22. An osmotically driven dispensing device for continuously delivering a beneficial agent to an environment of use at a predetermined rate profile, the device comprising:

a) a syringe housing having a movable piston therein, the piston dividing the syringe housing into a beneficial agent-containing compartment and a driving compartment;

b) an osmotic engine adjacent said driving compartment, said osmotic engine comprising a shaped wall surrounding a means for forming a driving fluid and a passageway through the wall for delivering the driving fluid from the engine into the driving compartment, at least a portion of the wall being comprised of a material that is permeable to the external liquid, the wall having a sufficient degree of impermeability to an osmotic solute within the engine to generate an osmotic pressure differential across the wall when the wall is exposed to the external liquid;

wherein the means for forming a driving fluid comprises a bilayered tablet having a layer of a gas generating means and a layer of an osmotic solute which generates no gas, said osmotic solute selected from the group consisting of osmotically active salts, acids and carbohydrates, whereby the external liquid permeates through the wall portion and causes the gas generating means to generate a gas, the gas being a first driving fluid which is pumped from the engine and through the passageway at a first rate over a first period of time and subsequently the external liquid permeates through the wall portion and forms a solution of the solute, the solution being a second driving fluid which is pumped from the engine and through the passageway at a second rate over a second period of time which follows the first period of time, the second rate being unequal to the first rate.

23. The device of claim 22, wherein the gas generating means comprises an effervescent couple.

24. The device of claim 22, wherein the gas generating means comprises a solid acidic material and a solid basic material that dissolve in the external liquid and react to form a gas.

25. The device of claim 24, wherein the gas produced by the gas generating means is carbon dioxide.

26. The device of claim 17 or 22, wherein the wall is comprised entirely of a material that is permeable to the external fluid.

27. The device of claim 17 or 22, wherein the wall is comprised of a cellulose ester.

28. The device of claim 17 or 22, wherein the osmotic solute is selected from the group consisting of sodium chloride, potassium chloride, glucose and lactose.

29. The device of claim 17 or 22, including a rigid non-dissolving ring-shaped wall support having a plurality of longitudinally extending grooves providing an open fluid flow path extending from the semipermeable wall portion toward the passageway through the wall.

30. The device of claim 22, wherein the layer of the osmotic solute further comprises a first solute and a second solute, said first and second solutes having differing solubilities in the external liquid.

31. The device of claim 17 or 22, wherein the environment of use is a human body.

* * * * *

UNITED STATES PATENT AND TRADEMARK OFFICE
CERTIFICATE OF CORRECTION

PATENT NO. : 5,312,389
DATED : May 17, 1994
INVENTOR(S) : Felix Theeuwes and Su Il Yum It is certified that error appears in the above-indentified patent and that said Letters Patent is hereby corrected as shown below:

column 16, line 25, insert after comprises --a bilayered tablet having a layer of a gas gnerating means and a layer of--.

Signed and Sealed this

Twenty-fifth Day of April, 1995

Attest:

BRUCE LEHMAN

Attesting Officer    Commissioner of Patents and Trademarks